United States Patent [19]

Watjen et al.

[11] Patent Number: 5,116,841
[45] Date of Patent: May 26, 1992

[54] IMIDAZOQUINOXALINES AND THEIR PREPARATION AND USE

[75] Inventors: Frank Watjen; Holger C. Hansen, both of Vaerlose, Denmark

[73] Assignee: Novo Nordisk A/S, Bagsvaerd, Denmark

[21] Appl. No.: 615,707

[22] Filed: Nov. 20, 1990

[30] Foreign Application Priority Data

Nov. 22, 1989 [DK] Denmark .................. 5884/89

[51] Int. Cl.⁵ .................. A61K 31/495; C07D 487/04
[52] U.S. Cl. .................. 514/250; 544/346
[58] Field of Search .................. 544/346; 514/250

[56] References Cited

U.S. PATENT DOCUMENTS 4,968,682  11/1990  Hansen .................. 544/346

Primary Examiner—Mark L. Berch
Attorney, Agent, or Firm—Steve T. Zelson; Elias Lambiris

[57] ABSTRACT

New imidazoquinoxaline compounds having the general formula I

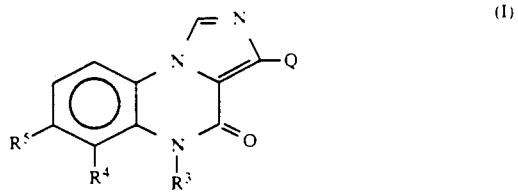

wherein

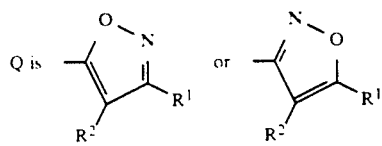

wherein $R^1$ and $R^2$ independently are hydrogen, straight or branched $C_{1-6}$-alkyl, or $C_{3-7}$-cycloalkyl; $R^3$ is hydrogen, straight or branched $C_{1-6}$-alkyl, straight or branched $C_{2-6}$-alkenyl, or aralkyl or aroylalkyl which may optionally be substituted with halogen or $C_{1-6}$-alkoxy; $R^4$ amd $R^5$ independently are hydrogen, halogen, $C_{1-6}$-alkyl or trifluoromethyl.

The compounds are useful in psychopharmaceutical preparations as anticonvulsants, anxiolytics, hypnotics and in improving the cognitive function of the brain of mammals.

7 Claims, No Drawings

IMIDAZOQUINOXALINES AND THEIR PREPARATION AND USE

The present invention relates to therapeutically active imidazoquinoxaline compounds, a method of preparing the same, pharmaceutical compositions comprising the compounds, and to methods of treating therewith. The novel compounds are useful in psychopharmaceutical applications, e.g., in the treatment of central nervous system ailments, for example, as anticonvulsants or anxiolytics.

It is well known (Squires, R. F. and Braestrup, C. in Nature (London) 266 (1977) 732-734) that specific sites in the central nervous systems of vertebrates exhibit a high specific affinity for binding 1,4- and 1,5-benzodiazepines. These sites are called benzodiazepine receptors.

It has now been found that members of a novel group of imidazoquinoxaline compounds have strong affinity for the benzodiazepine receptors which make them useful in psychopharmaceutical preparations.

Accordingly, it is an object of the invention to provide such novel imidazoquinoxaline compounds.

The imidazoquinoxaline compounds having the general formula I wherein

Q is  or wherein $R^1$ and $R^2$ independently are hydrogen, straight or branched $C_{1-6}$-alkyl, or $C_{3-7}$-cycloalkyl; $R^3$ is hydrogen, straight or branched $C_{1-6}$-alkyl, straight or branched $C_{2-6}$-alkenyl, or aralkyl or aroylalkyl which may optionally be substituted with halogen or $C_{1-6}$-alkoxy; and $R^4$ and $R^5$ independently are hydrogen, halogen, $C_{1-6}$-alkyl or trifluoromethyl.

The invention also relates to a method of preparing the above mentioned compounds. This method comprises:

a) reacting a compound of formula II (II)

wherein $R^3$, $R^4$ and $R^5$ have the meanings set forth above and wherein Y is a leaving group, with a compound having the formula III $$CN-CH_2-Q \quad (III)$$

wherein Q has the meaning set forth above, to form a compound of formula I, or b) reacting a compound of formula IV (IV)

wherein $R^1$, $R^2$, $R^3$, $R^4$ and $R^5$ have the meanings set forth above, with hydroxylamine to form either a mixture of V and VI or only the one or the other of V or VI (V)

(VI)

wherein $R^1$, $R^2$, $R^3$, $R^4$ and $R^5$ have the meanings set forth above, or c) reacting a compound of the formula V (V)

wherein $R^1$, $R^2$, $R^3$, $R^4$ and $R^5$ have the meanings set forth above with catalytic amounts of acid to form a compound of the formula I wherein Q is wherein $R^1$ and $R^2$ have the meanings set forth above, or d) reacting a compound of the formula VI

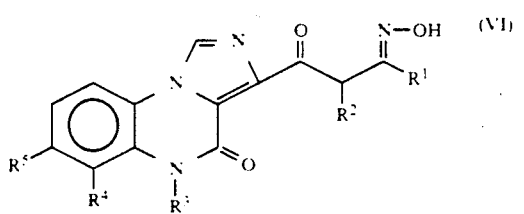

wherein $R^1$, $R^2$, $R^3$, $R^4$, and $R^5$ have the meanings set forth above with catalytic amounts of acid to form a compound of the formula I wherein Q is

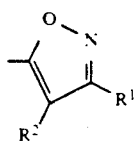

wherein $R^1$ and $R^2$ have the meanings set forth above, or e) reacting a compound of the formula VII

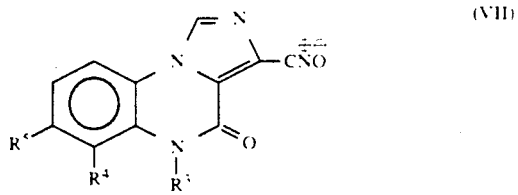

wherein $R^3$, $R^4$, and $R^5$ have the meanings set forth above with an alkene, alkyne or an equivalent thereof to form a compound of the formula I, wherein Q is

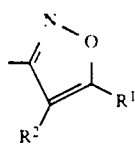

wherein $R^1$ has the meaning set forth above and $R^2$ is hydrogen, or f) dealkylating a compound of the formula VIII

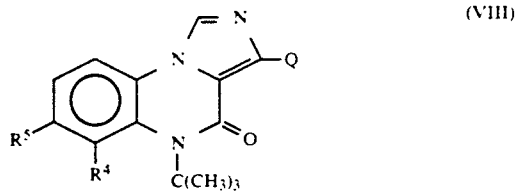

wherein $R^4$ and $R^5$ have the meaning set forth above and wherein Q is

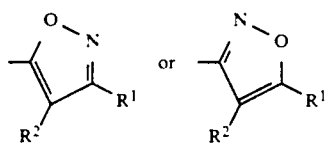

wherein $R^1$ and $R^2$ have the meanings set forth above to form a compound of the formula IX

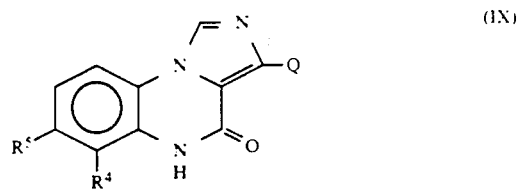

wherein Q, $R^4$ and $R^5$ have the meanings set forth above, or g) alkylating a compound of the formula IX wherein Q, $R^4$ and $R^5$ have the meanings set forth above with an alkyl halide to form a compound of formula I

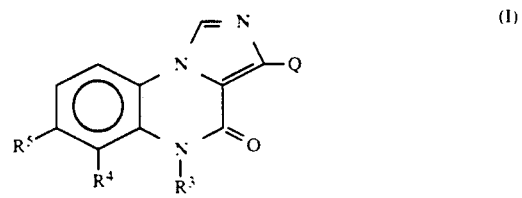

wherein Q, $R^3$, $R^4$ and $R^5$ have the meanings set forth above.

The leaving group, Y, may be any suitable leaving group and, for example, those disclosed in U.S. Pat. Nos. 4,031,079 or 4,359,420, for example, halogen, alkylthio, e.g., methylthio, aralkylthio, N-nitrosoalkylamino, alkoxy, mercapto, $-OP(O)(OR)_2$ wherein R is lower-alkyl or $-OP(O)(NR'R'')_2$ wherein R' and R'' each represents lower-alkyl or phenyl, or together with the nitrogen atom to which they are attached represent a heterocyclic radical such as morpholino, pyrrolidino, piperidino, or methylpiperazino. The reaction is preferably carried out under alkaline conditions, i.e., in the presence of a base, and among bases alkali metal, e.g., potassium or sodium, alkoxides or hydrides are preferred. The reaction is preferably conducted in the presence of an organic solvent which is nonreactive with the reactants and products of reaction under the conditions of reaction, especially an anhydrous solvent and preferably an anhydrous aprotic solvent such as dimethylformamide (DMF) or the like. The temperature range employed may be any range suitable for the reaction to proceed at a reasonable rate and without undue delay or decomposition and a range from a minus forty ($-40$) degrees Celsius to about room temperature is accordingly usually particularly suitable.

The starting materials may be prepared from commercially available organic compounds and by using well known synthetic methods.

The pharmaceutical properties of the compounds of the invention can be illustrated by determining their capability for displacing radioactive labelled flunitrazepam from benzodiazepine receptors.

The displacement activity of the compounds of the invention may be found by determining the ED50 value. The ED50 value represents the dose (mg/kg) of a test substance which causes the specific binding of flunitrazepam to benzodiazepine receptors in a living brain to be reduced to 50% of the control value.

Such an in vivo test is carried out as follows:

Principle. Twenty minutes after a dose of $^3$H-flunitrazepam ($^3$H-FNM) (200 μCi/kg, i.v.) the amount of specific $^3$H-FNM binding to brain benzodiazepine receptors has reached its maximal value. This specific binding of $^3$H-FNM can be partly or completely prevented by simultaneous or prior administration of pharmacologically active benzodiazepines and by some benzodiazepine-like agents (Chang and Snyder, Eur.J. Pharmacol. 48, 212–218 (1978)).

Test procedure. Suspensions of test substances (2 mg/ml) are prepared in 5% Duphasol-X (TM Duphar, castor oil-ethylene oxide derivative for emulsifying and solubilizing oil and other water-insoluble substances) by sonification for 10 min using a Branson B15 microtip ultrasonifier (setting 7). Groups of three mice (female, NMR, 18–22 grams) are injected with the test substance at 100. mg/kg intraperitoneally. Fifteen minutes after test substance administration the mice are challenged with 4 μCi intravenously of $^3$H-FNM (70–90) Ci/mole) in 200 μl physiological saline. Twenty minutes after $^3$H-FNM administration the mice are sacrificed by decapitation, the forebrains rapidly excised (within 30 sec) and homogenized in 12 ml of icecold 25 mM $KH_2PO_4$, pH 7.1, using an Ultra-Turrax homogenizer fitted with an N 10 shaft. Two aliquots of 1 ml are immediately filtered through Whatman GF/C glassfibre filters and washed with $2 \times 5$ ml of the above mentioned buffer. The amounts of radioactivity on the filters are determined by conventional scintillation counting. One group of untreated mice serves as control. One to three mice are injected with 25 μg/kg clonazepam i.p. 30 minutes before H-FNM to determine the amount of non-specific $^3$H-FNM binding, which should be between 8–15% of total binding. When doses of 100 mg/kg inhibit more than 50% of specific $^3$H-flunitrazepam binding; test substances are administered in doses, which are factors of 3.16 times lower than 100 mg/kg. The $ED_{50}$ for a test substance is defined as that dose which inhibits 50% of specific $^3$H-FNM binding. Specific binding is the amount of binding in controls minus the amount binding in clonazepam-treated mice.

Results. The $ED_{50}$ value is determined from dose response curves. If only one dose of test substance is administered the $ED_{50}$ value is calculated as follows, provided that the inhibition of specific binding is within the range of 25–75%:

$$ED_{50} = (\text{administered dose}) \cdot \frac{1}{\left[\frac{C_o}{C_x} - 1\right]} \text{ mg/kg}$$

where $C_o$ is specific binding in controls and $C_x$ is specific binding in mice treated with test substance.

Test results obtained by testing some compounds of the invention will appear from the following table I.

TABLE 1

| Compound | $ED_{50}$ (mg/kg) |
|---|---|
| Compound 29 | 0.37 |
| Compound 27 | 0.45 |
| Compound 8 | 1.8 |

The compound of the invention, together with a conventional adjuvant, carrier, or diluent, and if desired in the form of a pharmaceutically-acceptable acid addition salt thereof, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective central nervous system ailment alleviating amount of the active ingredient commensurate with the intended daily dosage range to be employed. Tablets containing one (1) milligram of active ingredient or, more broadly, one (1) to thirty (30) milligrams, per tablet, are accordingly suitable representative unit dosage forms.

The compounds of this invention can thus be used for the formulation of pharmaceutical preparations, e.g., for oral and parenteral administration to mammals including humans, in accordance with conventional methods of galenic pharmacy.

Conventional excipients are such pharmaceutically acceptable organic or inorganic carrier substances suitable for parenteral or oral application which do not deleteriously react with the active compound.

Examples of such carriers are water, salt solutions, alcohols, polyethylene glycols, polyhydroxyethoxylated castor oil, gelatin, lactose, amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxilliary agents such as lubricants, preservatives, stabilizers, wetting agents, emulsifiers, salt for influencing osmotic pressure, buffers and/or coloring substances and the like, which do not deleteriously react with the active compound.

For parenteral application, particularly suitable are injectable solutions or suspensions, preferably aqueous solutions with the active compound dissolved in polyhydroxylated castor oil.

Ampoules are convenient unit dosage forms.

For oral application, particularly suitable are tablets, dragees, or capsules having talc and/or a carbohydrate carrier or binder or the like, the carrier preferably being lactose and/or corn starch and/or potato starch. A syrup, elixir or like can be used when a sweetened vehicle can be employed. Generally, as to broader ranges, the compounds of the invention are dispensed in unit dosage form comprising 0.05–100 mg in a pharmaceutically-acceptable carrier per unit dosage.

A typical tablet which may be prepared by conventional tabletting techniques contains:

Active compound: 1.0 mg
Lactosum: 67.8 mg Ph.Eur.
Avicel ® 31.4 mg
Amberlite ® IRP 88: 1.0 mg
Magnesii stearas: 0.25 mg Ph.Eur.

Due to their high degree of affinity for the benzodiazepin receptors, the compounds of the invention are extremely useful in the treatment of central nervous system ailments or disorders, when administered in an amount effective for the alleviation, amelioration, or elimination thereof. The important CNS activity of the compounds of the invention includes both anticonvulsant and anxiolytic activities along with a low toxicity, together presenting a most favorable therapeutic index. The compounds of the invention may accordingly be administered to a subject, e.g., a living animal or a human body, in need of the same for the treatment, alleviation, amelioration, or elimination of an indication, associated with the central nervous system and the so-called benzodiazepin receptors, which requires such psychopharmaceutical treatment, e.g., especially convulsion and/or anxiety states, if desired in the form of a pharmaceutically-acceptable acid addition salt thereof (such as the hydrobromide, hydrochloride, or sulfate, in any event prepared in the usual or conventional manner, e.g., evaporation to dryness of the free base in solution together with the acid), ordinarily concurrently, simultaneously, or together with a pharmaceutically-acceptable carrier or diluent, especially and preferably in the form of a pharmaceutical composition thereof, whether by oral, rectal, or parenteral (including subcutaneous) route, in an effective psychopharmaceutical central nervous system ailment alleviating amount, e.g., an anticonvulsant and/or anxiolytic amount, and in any event an amount which is effective for the alleviation of such a central nervous system ailment due to their benzodiazepine receptor affinity. Suitable dosage ranges are 1–200 milligrams daily, 1–100 milligrams daily, and especially 1–30 milligrams daily, depending as usual upon the exact mode of administration, form in which administered, the indication toward which the administration is directed, the subject involved and the body weight of the subject involved, and the preference and experience of the physician or veterinarian in charge.

The invention will now be described in further detail with reference to the following examples:

EXAMPLE 1

The 1,3-diketones were processed into the monooximes by reaction with hydroxylamine. The 1 and 3 position isomers could be separated by column chromatography (SiO$_2$/CH$_2$Cl$_2$: acetone, 4:1). In many reactions only one isomer was formed.

In a typical experiment a mixture of the 1,3-diketone (5 mmol), hydroxylammonium chloride (10 mmol) and K$_2$CO$_3$ (10 mmol) was stirred in methanol (50 ml) at room temperature or at reflux temperature. The reaction was followed by TLC. After completion of the reaction, the solvent was removed in vacuo and the residue was treated with water. This treatment left the monooxime as a crystalline precipitate. In cases where both position isomers were formed, column chromatography was undertaken in order to separate the position isomers (identification of the isomers was done on basis of the MS fragmentation).

The following monooximes were obtained from the corresponding diketones:

3-(3-cyclopropyl-1-hydroximino-3-oxopropyl)-4,5-dihydro-5-isopropyl-4-oxo-imidazo[1,5-a]quinoxaline, m.p. 235°–236° C. (Compound 1).

5-tert-butyl-4,5-dihydro-3-(1-hydroximino-3-oxobutyl)-4-oxoimidazo[1,5-a]quinoxaline, m.p. 381°–382° C. decomp. (Compound 2).

5-tert-butyl-4,5-dihydro-3-(3-hydroximino-1-oxobutyl)-4-oxo-imidazo[1,5-a]quinoxaline, m.p. 174°–177° C. (Compound 3).

4,5-dihydro-3-(3-hydroximino-1-oxobutyl)-5-isopropyl-4-oxo-imidazo[1,5-a]quinoxaline, m.p. 246°–248° C. (Compound 4).

5-tert-butyl-3-(3-cyclopropyl-1-hydroximino-3-oxopropyl)-4,5-dihydro-4-oxo-imidazo[1,5-a]quinoxaline, m.p. 130°–132° C. (Compound 5).

6-chloro-3-(1-hydroximino-3-oxopropyl)-4,5-dihydro-5-methyl-4-oxo-imidazo[1,5-a]quinoxaline, m.p. 194°–196° C. (Compound 6).

3-(3-cyclopropyl-1-hydroximino-2-methyl-3-oxopropyl)-4,5-dihydro-5-isopropyl-4-oxo-imidazo[1,5-a]quinoxaline, m.p. 195°–199° C. (Compound 7).

The described monooximes were dehydrated to their corresponding isoxazoles with the aid of catalytic amounts of hydrochloric acid in ethanol. In case of compounds having a tert-butyl group in the 5-position, the reaction was carried out at room temperature, otherwise elimination of isobutylene took place.

EXAMPLE 2

Method A 3-(5-cyclopropyl-3-isoxazolyl)-4,5-dihydro-5-isopropyl-4-oxo-imidazo[1,5-a]quinoxaline To a suspension of 3-(3-cyclopropyl-1-hydroximino-3-oxopropyl)-4,5-dihydro-5-isopropyl-4-oxo-imidazo[1,5-a]quinoxaline (0.3 g) in ethanol (25 ml) was added one drop of 4 M hydrochloric acid and the mixture was heated at reflux for 10 min. Cooling the resulting solution to room temperature gave the title compound as a white crystalline precipitate, which was collected by filtration and dried. M.p. 247°–249° C. (Compound 8).

In the same manner the following isoxazoles were obtained:

5-tert-butyl-4,5-dihydro-3-(3-methyl-5-isoxazolyl)-4-oxoimidazo[1,5-a]quinoxaline, m.p. 391° C. (Compound 9).

5-tert-butyl-4,5-dihydro-3-(5-methyl-3-isoxazolyl)-4-oxoimidazo[1,5-a]quinoxaline, m.p. 128°–130° C. (Compound 10).

4,5-dihydro-5-isopropyl-3-(3-methyl-5-isoxazolyl)-4-oxoimidazo[1,5-a]quinoxaline, m.p. 291°–292° C (Compound 11).

6-chloro-3-(5-cyclopropyl-3-isoxazolyl)-4,5-dihydro-5-methyl-4-oxo-imidazo[1,5-a]quinoxaline, m.p. 232°–233° C. (Compound 12).

5-tert-butyl-3-(5-cyclopropyl-3-isoxazolyl)-4,5-dihydro-4-oxo-imidazo[1,5-a]quinoxaline, m.p. 187°–188° C. (Compound 13).

3-(5-cyclopropyl-4-methyl-3-isoxazolyl)-4,5-dihydro-5-isopropyl-4-oxo-imidazo[1,5-a]quinoxaline, m.p. 180°–182° C. (Compound 14).

Method B 5-formylaminomethyl-3-methylisoxazole

A stirred solution of nitroethane (17.9 ml, 0.25 mol) in N,N-dimethylacetamide (DMA) (250 ml) was added dropwise at 25°–30° C. to a solution of sodium methoxide, prepared by dissolving sodium (5.75 g) in dry methanol. The reaction mixture was cooled to 5° C. and acetyl chloride (18.5 ml, 0.26 mol) was added at 5°–10° C. Then was added a solution of 3-formylaminopropyn (17 g, 0.20 mol) in DMA (15 ml), and stirring was continued at room temperature overnight. The solvent was removed in vacuo and the residue was extracted with ether (300 ml). The ether was evaporated leaving an oily residue from which the title compound was isolated by distillation (120°–140° C./0.3 mmHg); $^1$H-NMR (CDCl$_3$) 2.21 (s,3H), 4.35 (d,2H), 5.97 (s,1H), 7–8 (br, 1H), 8.13 (s,1H). (Compound 15).

5-isocyanomethyl-3-methylisoxazole

To a cooled and stirred solution of 5-formylaminomethyl-3-methylisoxazole (5.45 g, 39 mmol) and triethylamine (16.7 ml, 120 mmol) in dichloromethane (50 ml) was added dropwise phosphorus oxychloride (4 ml, 43 mmol) during 30 min., the temperature being kept below 0° C. Stirring was continued for 30 min., then a solution of sodium carbonate (4.55 g, 43 mmol) in water (50 ml) was added dropwise (<0° C.). Additional water (50 ml) was added and the layers were separated. The aqueous phase was extracted twice with dichloromethane (2×30 ml). The combined organic layers were dried, the solvent was evaporated, and the residue was extracted with ether (2×75 ml). The extracts were combined and the solvent was removed to give the title compound as a dark oil. $^1$H-NMR (CDCl$_3$): 2.30 (s,3H), 4.75 (s,2H), 6.25 (s,1H). (Compound 16).

5-tert-butyl-4,5-dihydro-3-(3-methyl-5-isoxazolyl)-4-oxoimidazo[1,5-a]quinoxaline To a stirred solution of 1-tert-butyl-1,2,3,4-tetrahydro-2,3-dioxoquinoxaline (6.54 g, 30 mmol) in dry dimethylformamide (DMF) (30 ml) under nitrogen was added sodium hydride (80% in oil, 9.6 g, 32 mmol). After stirring for 10 min. the solution was cooled to −20° C. and diethyl chlorophosphate (5.6 ml, 39 mmol) was added. The mixture was allowed to reach room temperature and then cooled to −30° C., whereafter 5-isocyanomethyl-3-methylisoxazole (3.0 g, 25 mmol) and finally a solution of potassium tert-butoxide (3.0 g, 26 mmol) in dry DMF (30 ml) was added keeping the temperature below −20° C. The reaction mixture was warmed to room temperature, acidified with acetic acid (1 ml) and evaporated in vacuo. The residue was triturated with water and ether, and the resulting precipitate was filtered off and partitioned between 0.5 M aqueous sodium hydroxide (50 ml) and dichloromethane (50 ml). The organic layer was filtered through celite, dried, and evaporated to give the title compound, m.p. 395° C. (Compound 17).

EXAMPLE 3

4,5-dihydro-3-(3-methyl-5-isoxazolyl)-4-oxo-imidazo[1,5-a]quinoxaline

A stirred suspension of 5-tert-butyl-4,5-dihydro-3-(3methyl-5isoxazolyl)-4oxo-imidazo[1,5-a]quinoxaline (0.65 g) in a mixture of ethanol (10 ml) and 4 M hydrochloric acid (1 ml) was refluxed for 10 min. Then the mixture was cooled to room temperature and water (10 ml) was added. The precipitated product was collected by filtration and dried to give the title compound as a white solid, m.p. 393° C. (Compound 18).

EXAMPLE 4

4,5-dihydro-5-ethyl-3-formyl-4-oxo-imidazo[1,5-a]quinoxaline

To a stirred −70° C. cold solution of ethyl 4,5-dihydro-5-ethyl-4-oxo-imidazo[1,5-a]quinoxaline-3-carboxylate (800 mg, 2.5 mmol) in dry THF was added dropwise a 1 M toluene solution of diisobutylaluminiumhydride (4 ml). Stirring at −70° C. was continued for 40 min., whereafter methanol (2 ml) was added. The reaction mixture was then extracted at ambient temperature between water/CH$_2$Cl$_2$. The organic phase was dried and evaporated, whereafter the residue was treated with ethyl acetate. This treatment left a crystalline precipitate of the title compound. The crystals were filtered off and washed with ethyl acetate, m.p. 259°-260° C. (Compound 19).

In the same manner was prepared 4,5-dihydro-3-formyl-5-isobutyl-4-oxo-imidazo[1,5-a]quinoxaline, m.p. 239°-240° C. from reduction of ethyl 4,5-dihydro-5-isobutyl-4-oxoimidazo[1,5-a]quinoxaline-3-carboxylate. (Compound 20).

EXAMPLE 5

4,5-dihydro-5-ethyl-4-oxo-imidazo[1,5-a]quinoxaline-carbaldoxime

A mixture of 4,5-dihydro-5-ethyl-3-formyl-4-oxo-imidazo[1,5-a]quinoxaline (1.5 g, 6 mmol) and NH$_2$OH.HCl (1 g, 14 mmol) was stirred in methanol (30 ml). pH was adjusted to 11 by addition of triethylamine. After stirring for 1 h the reaction was completed, and the solvent was removed by evaporation. The residue was treated with water (50 ml). This left a crystalline precipitate of the title compound, which was filtered off and washed with water, m.p. 272°-273° C. (Compound 21).

In a similar manner was prepared 4,5-dihydro-5-isobutyl-4-oxo-imidazo[1,5-a]quinoxaline-3-carbaldoxime, m.p. 273°-278° C. (Compound 22).

EXAMPLE 6

5-ethyl-4,5-dihydro-3-(5-methoxymethyl-3-isoxazolyl)-4-oxo-imidazo[1,5-a]quinoxaline To a suspension of 4,5-dihydro-5-ethyl-4-oxo-imidazo[1,5-a]quinoxaline-3-carbaloxime (0.5 g, 2 mmol) in DMF (20 ml) was added a solution of N-bromosuccinimide (NBS) (0.35 g, 2 mmol) in DMF (10 ml) and the mixture was stirred at room temperature for 1 h. Then propargyl methyl ether (0.25 ml, 3 mmol) and triethylamine (0.56 ml, 4 mmol) was added, and stirring was continued overnight. The solvent was removed in vacuo and the residue was triturated with water and ethyl acetate. The precipitate was collected by filtration and purified chromatographically on silica gel-/acetonedichloromethane (1:4) to give the title compound, m.p. 195°-196° C. (Compound 23).

Similarly, 4,5-dihydro-5-ethyl-4-oxo-imidazo[1,5-a]quinoxaline-3-carbaldoxime was brought to react with NBS and trimethylsilylacetylene/triethylamine. The resulting reaction mixture was hydrolysed by treatment with sodium hydroxide (2 molar euivalents 4 M solution) to give, after chromatographic purification (SiO$_2$-/ethyl acetate), 5-ethyl-4,5-dihydro-3-(3-isoxazolyl)-4-oxo-imidazo[1,5-a]quinoxaline, m.p. 246°-248° C. (Compound 24).

EXAMPLE 7

4,5-dihdydro-5-isobutyl-3-(5-methyl-3-isoxazolyl)-4-oxoimidazo[1,5-a]quinoxaline A solution of NBS (0.35 g, 2 mmol) in dry DMF (5 ml) was added to a stirred suspension of 4,5-dihydro-5-isobutyl-4-oxo-imidazo[1,5-a]quinoxaline-3-carbaldoxime (0.6 g, 2 mmol) in dry DMF (15 ml) at room temperature. After 1.5 h was added 2-bromopropene (0.26 ml, 3 mmol) and triethylamine (1.1 ml, 8 mmol). After 5 days water (approx. 50 ml) was added, and the solid which precipitated was collected by filtration. From this crude product the title compound was isolated by extraction with ethyl acetate (30 ml) and purification of the extract by column chromatography (SiO$_2$/ethyl acetate) giving pale crystals. m.p. 213°–215° C. (Compound 25).

EXAMPLE 8

4,5-dihydro-5-methyl-3-(3-methyl-5-isoxazolyl)-4-oxoimidazo[1,5-a]quinoxaline To a stirred suspension of 4,5-dihydro-3-(3-methyl-5-isoxazolyl)-4-oxo-imidazo[1,5-a]quinoxaline (150 mg, 0.56 mmol) in dry DMF (10 ml) was added sodium hydride (80% in mineral oil, 24 mg). After 10 min. was added an excess of iodomethane (0.1 ml, 1.6 mmol) and the mixture was stirred for 2.5 h. Upon addition of water (30 ml) the compound precipitated and was filtered off and dried. m.p. 302° C. (Compound 26).

With 4,5-dihydro-3-(3-methyl-5-isoxazolyl)-4oxo-imidazo-[1,5-a]quinoxaline and appropriate halides as starting materials and DMF as solvent, the following compounds were prepared:

4,5-dihydro-5-(3-methoxybenzyl)-3-(3-methyl-5-isoxazolyl)-4-oxo-imidazo[1,5-a]quinoxaline, m.p. 222°–224° C., by alkylation with 3-methoxybenzyl chloride. (Compound 27).

4,5-dihydro-3-(3-methyl-5-isoxazolyl)-4-oxo-5-phenacylimidazo[1,5-a]quinoxaline, m.p. 325° C., by alkylation with phenacyl bromide. (Compound 28).

4,5-dihydro-5-(3,3-dimethylallyl)-3-(3-methyl-5-isoxazolyl)-4-oxo-imidazo[1,5-a]quinoxaline, m.p. 257°–259° C., by alkylation with 3,3-dimethylallyl bromide. (Compound 29).

I claim:

1. A compound of formula I

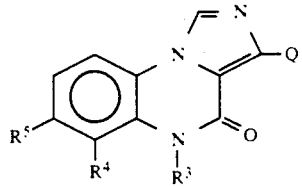

wherein

Q is 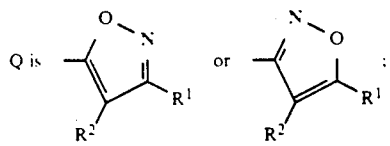

$R^1$ and $R^2$ independently are hydrogen, straight or branched $C_{1-6}$-alkyl or $C_{3-7}$-cycloalkyl;

$R^3$ is hydrogen, straight or branched $C_{1-6}$-alkyl, straight or branched $C_{2-6}$-alkenyl, or aralkyl or aroylalkyl, the latter two may be optionally substituted with halogen or $C_{1-6}$-alkoxy; and $R^4$ and $R^5$ independently are hydrogen, halogen, $C_{1-6}$-alkyl or trifluoromethyl.

2. A compound which is 4,5-dihydro-5-(3,3-dimethylallyl)-3-(3-methyl-5-isoxazolyl)-4-oxo-imidazo[1,5-a]quinoxaline.

3. A compound which is 4,5-dihydro-5-(3-methoxybenzyl)-3-(3-methyl-5-isoxazolyl)-4-oxo-imidazo[1,5-a]quinoxaline.

4. A pharmaceutical composition comprising a compound according to claim 1 together with a pharmaceutically-acceptable carrier or diluent.

5. A pharmaceutical composition according to claim 4 in the form of an oral dosage unit containing 1–100 mg of the active compound.

6. A method of treating convulsions or anxiety in a subject in need thereof comprising administering to said subject an effective amount of a compound according to claim 1.

7. A method of treating convulsions or anxiety in a subject in need thereof comprising administering to said subject a pharmaceutical composition according to claim 4.

* * * * *